United States Patent [19]
Alfano et al.

[11] Patent Number: 5,710,429
[45] Date of Patent: Jan. 20, 1998

[54] ULTRAFAST OPTICAL IMAGING OF OBJECTS IN OR BEHIND SCATTERING MEDIA

[76] Inventors: Robert R. Alfano, 3777 Independence Ave.; Feng Liu, 3055 Bailey Ave., Apt. #E2, both of Bronx, N.Y. 10463; Quan-Zhen Wang, 552 Riverside Dr., Apt. 2G, New York, N.Y. 10027; Ping P. Ho, 24 W. Terrace Rd., Great Neck, N.Y. 11021; Leming M. Wang, 134-46 Maple Ave., Apt. 7B, Flushing, N.Y. 11355; Xiangchun Liang, 2670 Valentine Ave. Apt. #9, Bronx, N.Y. 10458

[21] Appl. No.: 419,623
[22] Filed: Apr. 6, 1995
[51] Int. Cl.[6] .................. G01N 21/49; G01N 21/59
[52] U.S. Cl. .................. 250/358.1; 250/330; 250/341.1
[58] Field of Search ................. 250/330, 332, 250/341.1, 358.1

[56] References Cited

U.S. PATENT DOCUMENTS 4,945,239  7/1990  Wist et al. .............. 250/358.1 X
5,140,463  8/1992  Yoo et al. ................ 359/559
5,371,368 12/1994  Alfano et al. ........... 250/341.1

OTHER PUBLICATIONS

Anderson et al., "Microscope Imaging Through Highly Scattering Media", Optics Letters, vol. 19, No. 13, Jul. 1, 1994, pp. 981–983.

Saleh et al., Fundamentals of Photonics, pp. 136–139, published by John Wiley & Sons, Inc., New York (1991).

Primary Examiner—Edward J. Glick
Attorney, Agent, or Firm—Kriegsman & Kriegsman

[57] ABSTRACT

A system for imaging an object in or behind a highly scattering medium includes a light source for illuminating the highly scattering medium with a beam of light. The light emerging form the highly scattering medium consists of a ballistic component, snake-like component and a diffuse component. A 4F Fourier imaging system including a Fourier spatial filter located at 2F is used to form a time gated image of the emerging light, the time gated image consisting primarily of the ballistic component and the snake-like component.

6 Claims, 8 Drawing Sheets

Time-gating using different shaped spatial filters

FIG. 6(a) NO FILTER

Experimental setup of a Kerr-Fourier time and spatial gated imaging system
ML: Nd+:glass mode-locked laser; BS: 1054nm/427nm beam splitter; P: calcite polarizer; A: analyzer (calcite polarizer); $L_1$ and $L_2$: lenses; Sample: soil solution cell with 50mm~thickness; K: $CS_2$ Kerr cell; FL: focusing lens. Mechanical stirrer with rotation rate of ~5 cycles/second was used to keep an approximately stable concentration of solution.

ical imaging techniques.

ULTRAFAST OPTICAL IMAGING OF OBJECTS IN OR BEHIND SCATTERING MEDIA

BACKGROUND OF THE INVENTION

The present invention relates to imaging methods and systems useful in the detection of objects in or behind a scattering media.

In U.S. Pat. No. 5,371,368 to Alfano et al there is disclosed a system for imaging an object in or behind a highly scattering medium which includes a laser for illuminating the highly scattering medium with a beam of light. The light emerging from the highly scattering medium consists of a ballistic component, a snake-like component and a diffuse component. A 4F Fourier imaging system with a Kerr gate located at 2F is used to form a time-space gated image of the emerging light, the time-space gated image consisting primarily of the ballistic component and the snake-like component.

Other patents and publications of interest include U.S. Pat. No. 5,140,463 to Yoo et al.; U.S. Pat. No. 4,945,239 to Wist et al.; U.S. Pat. No. 4,948,974 to Nelson et al; U.S. Pat. No. 4,807,637 to Bjorkolm; U.S. Pat. No. 4,707,128 to Coles; U.S. Pat. No. 4,174,524 to Moran; K. M. Yoo, F. Liu, and R. R. Alfano, Opt. Lett. 15, 320 (1990); L. Wang, P. Ho, C. Liu, G. Zhang, and R. R. Alfano, Science 253, 769 (1991); Fujimoto, S. De Silvestri, E. Ippen, C. Puliafito, R. Margolis and A. Oseroff, Science 254, 1178 (1991); H. Chen, Y. Chen, D. Dilworth, E. Leith, J. Lopex and J. Valdmanis, Opt. Lett. 16, 487 (1991); and S. Anderson-Engels, R. Berg, S. Svanberg, and O. Jarlman, Opt. Lett. 15, 1178 (1990).

SUMMARY OF THE INVENTION

It is an object of the present invention to provide a novel imaging technique useful in the detection of hidden objects in scattering media.

It is another object of the present invention to provide a transillumination imaging technique that can be used to detect objects in the submillimeter range.

According to one feature of the present invention, a Fourier spatial filter, i.e. a spatial filter at the Fourier plane, is used to temporally gate the light exiting the medium. The Fourier spatial filter improves image quality by filtering out the later arriving diffusive photons exiting the medium. In a preferred embodiment of the invention, the Fourier spatial filter comprises an aperture at the back focal plane of a lens used to collect the light emerging from the light scattering media.

According to another feature of the invention, the particular scattered light from the medium can be easily selected by simply changing the shape of the spatial filter.

According to still another feature of the invention, a Fourier filtering system is used for detecting objects in a variety of non-medical applications, such as, for example, environmental protection from industrial waste or oil spills.

Additional objects, features and advantages of the present invention will be set forth in part in the description which follows, and in part will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference characters represent like parts.

The solid, dashed, and dot-dashed curves show the temporal profiles of scattered pulse when the diameter of the spatial Fourier filter is 10, 3, and 1 mm, respectively. (a) 2 mm×10% Intralipid solution, (b) 50 mm×0.4% Intralipid solution.

DETAILED DESCRIPTION OF PREFERRED EMBODIMENTS

The present invention, according to one aspect, is directed to the discovery that a spatial Fourier gate can select the early light from the scattering or turbid media with picosecond (ps, $10^{-12}$ second) gating capability without the need for ultrafast time resolved detection instruments. This novel idea of Fourier spatial gating can be used to image objects hidden behind or inside a scattering media.

Imaging objects, defects, or abnormality hidden in highly scattering or turbid media using non-ionizing radiation has become very active because of its potential wide application to medical biological, aerospace, and environmental fields. Although X-ray techniques have been widely used to image biological, aerospace, and environmental subjects, X-ray radiation is ionizing and exposing to too much radiation is a safety hazard. It would be of great interest to use safe, non ionizing radiation, in particular, the highly developed visible and near infrared lasers, to image subjects using transillumination techniques. However, for many subjects of interest such as the human body, clouds, and soil, the light in visible and near infrared spectral region is highly scattered inside these subjects. Due to the scattering in these types of subjects, most of the light emerging there from is multiple scattered and travels in all angular directions if the subject is strong enough in scattering. Thus, an image (shadowgram) of the subject obtained by transillumination is degraded. Indeed, a useful image of the subject cannot be obtained by the conventional steady state transillumination imaging method when the subject is strong enough in scattering.

A light pulse propagating through a scattering medium is split into ballistic, snake, and diffusive components in the scattered signal. The ballistic component, which carries most direct information of medium structure, of the propagating signal, travels in a straight line path and emerges from the medium first in time. The snake component consists of the light that travels through the medium in paths slightly deviated from the straight line path. The snake component arrives next to the ballistic component in time. The diffusive photons are those multiple scattered in the scattering medium. The diffusive photons lose the direct information about the medium and contribute noise in the shadowgram. In a highly scattering medium the diffusive component is much stronger than the snake and ballistic components and the information cannot be transmitted successfully. To improve the ability to see through a highly scattering random media one needs to reduce the diffusive component. Various ultrafast time-gated methods have been applied to remove the diffusive noise component to improve the imaging quality.

This invention teaches a novel method of reducing diffusive photons using a spatial Fourier filter. The present invention is directed to the discovery that a steady state Fourier spatial filter acts as a time selector with ps time gating capability for light emerging from a scattering/turbid medium. The effect of the spatial filtering can be regarded as an early time passing gate since it gates out mostly the later arriving diffusive photons. This method can be used with either continuous wave (CW) illumination or ultrashort femtosecond (fs, $10^{-15}$ second) or ps light pulse illumination, and with and/or without time-resolved detection methods, such as Cross Correlation Second Harmonic Generation (fs) or streak camera (ps), to improve the image of objects hidden in the scattering medium.

Figure 1:
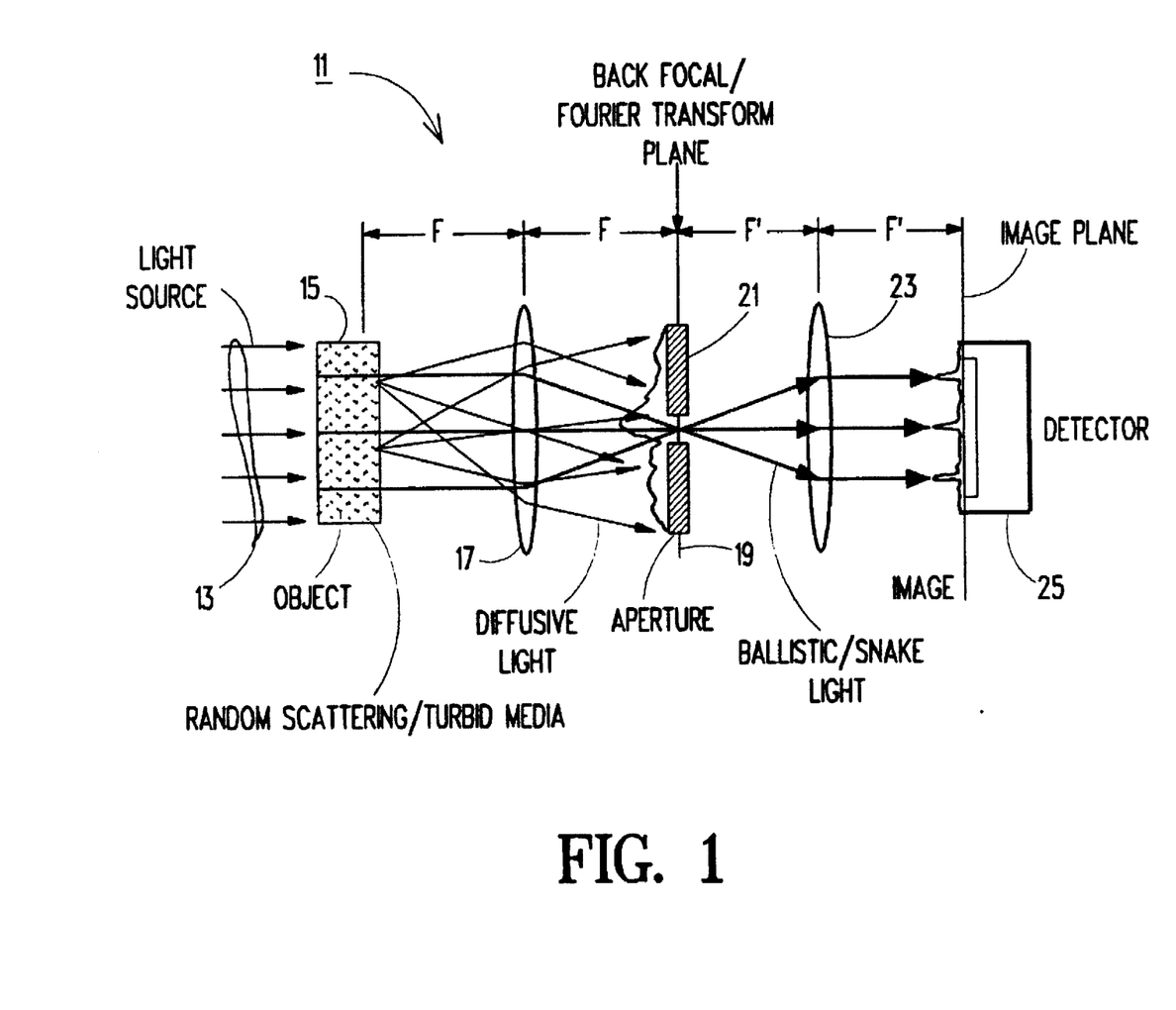
FIG. 1 is a schematic diagram illustrating the principle of Fourier spatial filtering of this invention.

Consider the transillumination imaging arrangement 11 shown in FIG. 1 wherein, a collimated beam of light 13 is incident on a highly scattering medium 15. The emerged/transmitted light is angle resolved by a lens 17, or as is commonly known is spatially Fourier transformed on the back focal (Fourier) plane 19 of lens 17. The forward straight traveling light which contains all the ballistic light and most of the snake light is transformed onto the center optical axis region (zero or low spatial frequency region) of the Fourier plane. The off angle traveling light is transformed onto the region away from the center (high spatial frequency region), the larger the angle off the optical axis, the further away from the region. Thus, the multiple scattered diffusive light which emerges from the medium traveling in all directions is angle resolved more or less uniformly on the Fourier plane, while the ballistic and snake components are resolved at the center of the Fourier plane. Therefore, a spatial filter 21 centered at the Fourier spectrum plane can filter out most of the diffusive component and allow the ballistic and snake components to pass through. The light that passes through filter 21 is collected by another lens 23 and detected by a photo detector 25. The later arriving diffusive photons can be greatly eliminated from the detection, and the Fourier spatial filtering can be regarded as a time gating unit. The time window is determined by the aperture size of filter 21. The image quality detected with the Fourier spatial filtering can be greatly improved as compared with the conventional transillumination method (same as without filtering).

Figure 2:
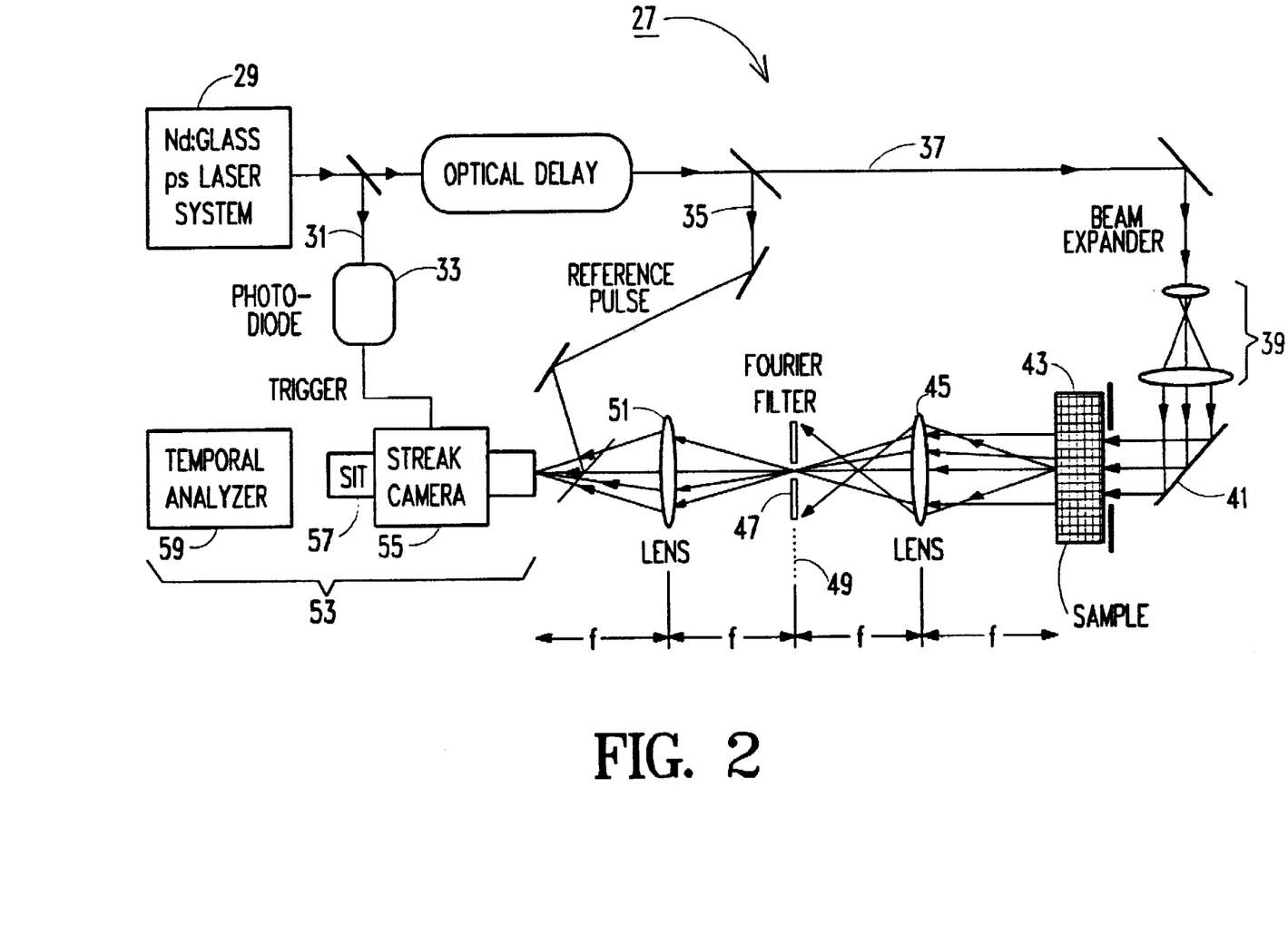
FIG. 2 is a schematic diagram of an experimental arrangement used to test the concept of this invention.

A schematic diagram of an experimental setup 27 to prove this novel idea of Fourier spatial gate as a temporal gate is shown in FIG. 2. A passive mode-locked laser system 29 with two stages of amplification generates laser pulses of 8 ps in pulse duration with approximately 100 uJ pulse energy at 527 nm. The output laser pulse was split into three beams. One of the beams 31 was converted to an electrical signal by a photodiode 33 which triggers the measurement instruments, another 35 was used as a reference pulse. The main beam 37 was expanded by a beam expander 39, deflected off a mirror 41 and incident on a cell 43 containing scattering sample (Intralipid solution). The output scattered laser pulse was collected with a lens 45 of 10 cm local length. A mechanical spatial filter 47 with variable size was placed at the Fourier plane 49 of the collecting lens. A second lens 51 with same focal length as lens 45 coupled the filtered signal into a ps streak camera system 53 made up of a streak camera 55, an SIT 57 and a temporal analyzer 59 to measure the temporal distribution.

Three different kinds of scattering samples were used in the investigation. The products of the Intralipid concentrations in the solutions and the sample lengths (nL) were kept constant for the three samples: (1)a 2 mm thick cell containing 10% Intralipid solution; (2)a 10 mm thick cell containing 2% Intralipid solution, and (3)a 50 mm thick cell containing 0.4% Intralipid solution.

Figure 3A:
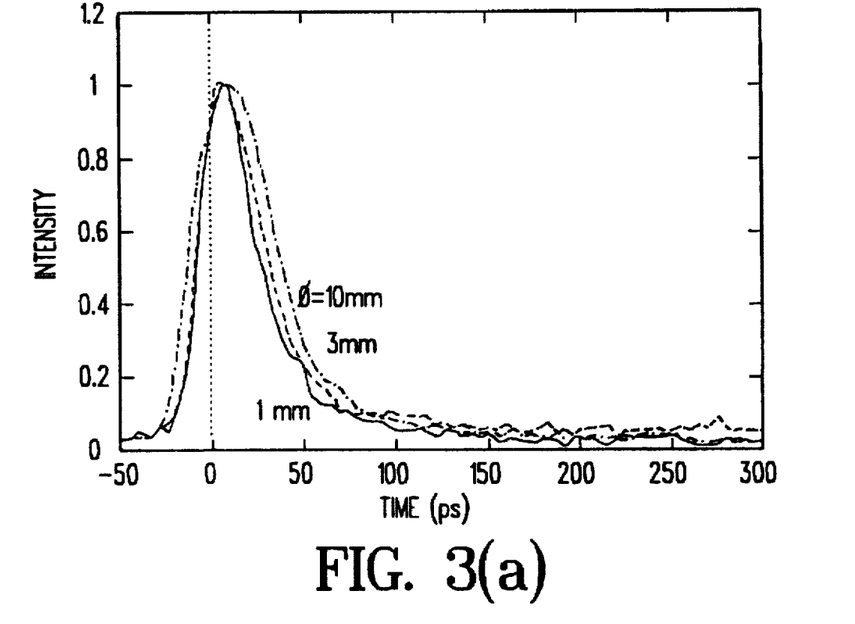
FIGS. 3(a) and 3(b) are a pair of graphs showing the temporal profiles of the spatially filtered laser pulses scattered by a scattering sample, namely, Intralipid solution in the arrangement shown in FIG. 2.
Figure 3B:
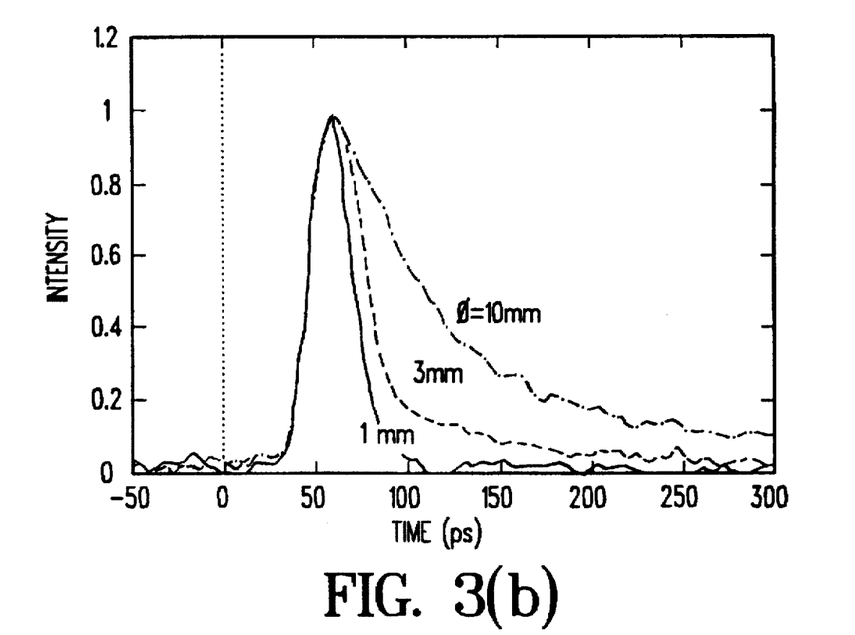

FIGS. 3(a) and 3(b) display the normalized temporal profiles of the scattered laser pulses propagated through the scattering Intralipid solutions with different sizes of spatial Fourier filters to show the time gating potential of the Fourier spatial gate. FIG. 3(a) shows the results for 2 mm×10% Intralipid solution. When the diameter of the spatial Fourier filter was 10 mm, the pulse duration of the scattered pulse was approximately 45 ps. When the diameter of the spatial Fourier filter was reduced to 3 mm, the pulse duration was reduced to 30 ps. When the diameter of the spatial filter was further reduced to 1 mm, the pulse duration of the measured scattered pulse was 22 ps which is close to 20 ps overall time resolution of the system.

FIG. 3(b) displays results from 50 mm×0.4% Intralipid solution. When the diameter of the spatial Fourier filter is 10 mm, the measured scattered pulse has a fast rising edge and a slow decay tail. The pulse duration of full-width-at-half-maximum (FWHM) is approximately 65 fs. When the diameter of the spatial Fourier filter is reduced to 3 mm, the slow decay tail of the scattered pulse is reduced and the FWHM pulse duration is reduced to 37 ps. When the diameter of the spatial Fourier filter was further reduced to 1 mm, the slow decay tail of the scattered pulse was further reduced and the FWHM pulse duration is reduced to 21 ps.

Figure 4:
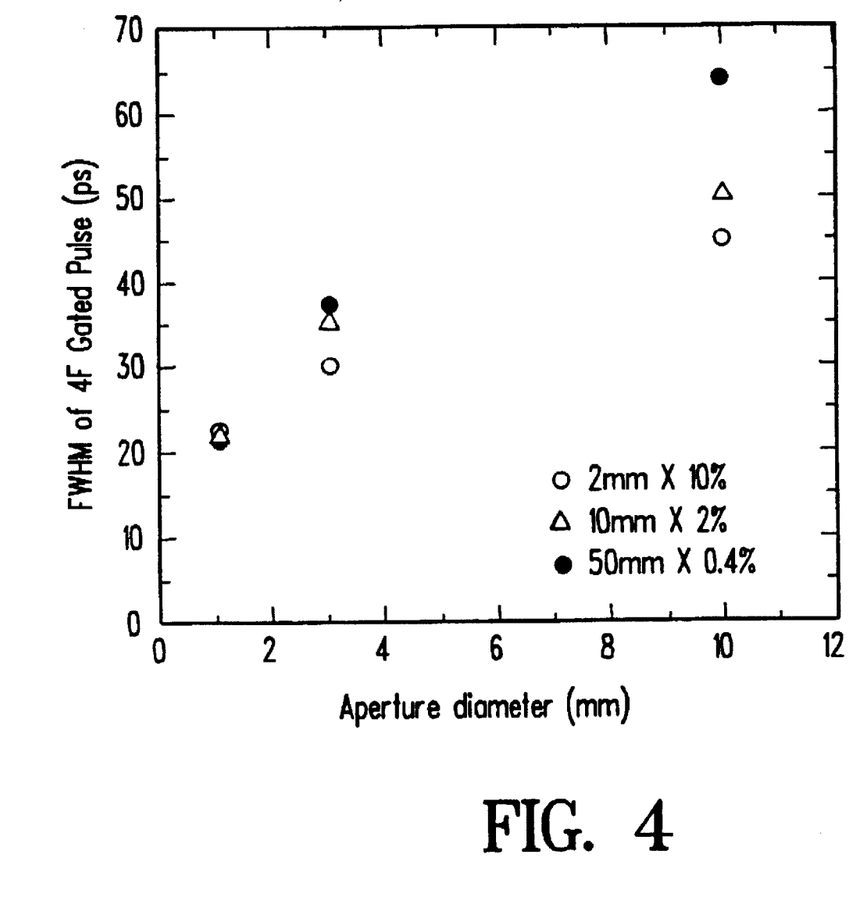
FIG. 4 is a graph showing the gated pulse duration of the scattered pulse as a function of aperture diameter size for the same sample length (nL): a 2 mm×10% Intralipid solution; a 10 mm×2% Intralipid solution; and a 50 mm×0.4% Intralipid solution in the arrangement shown in FIG. 2.

The results of the pulse narrowing by the spatial Fourier filter for all three samples are shown in FIG. 4. The pulse duration of the scattered pulses is reduced by a decreasing of the sizes of the spatial Fourier filters for all three samples. These results show that the spatial Fourier filter acts as a temporal gate for light propagating through scattering media and can be used to provide a good method to increase the signal to noise ratio for optical imaging of objects inside scattering/turbid. This unit will improve imaging using CW or pulse light sources. The spatial Fourier filter of the present invention may be an aperture of fixed size or of variable size positioned at the back focal plane of the lens. Preferably, the aperture has a diameter of 0.1 to 10 mm.

According to another aspect of the invention, a spatial filter at the Fourier plane can be used to remove certain sections of a scattered light pulse from a scattering media with the particular section being removed depending on the particular shape of the filter.

Referring now FIGS. 5(a) through 5(d), there are shown four different types of spatial filters to be placed at the Fourier plane as per this invention, namely: (a) an aperture 61; (b) its complementary inverse spatial filter 63; (c) a first type of ring-shaped spatial filter 65; and (d) a second type of ring-shaped spatial filter 67, respectively.

Figure 5A:
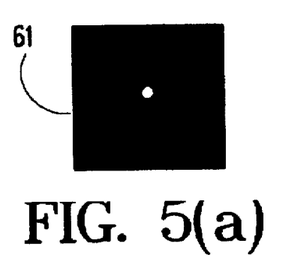
FIG. 5(a) through 5(d) are examples of different types of spatial Fourier filters according to another feature of this invention.
Figure 5B:
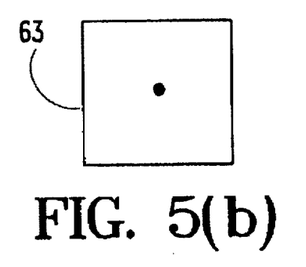
Figure 5C:
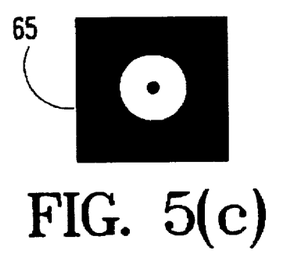
Figure 5D:
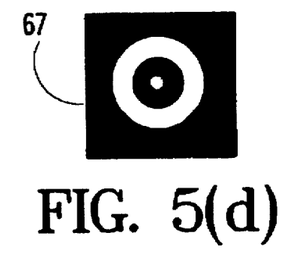

The spatial filter 61 in FIG. 5(a) placed at the Fourier plane removes the scattered light in later time. Its complementary (inverse) spatial Filter 63 in FIG. 5(b) will remove the ballistic and snake light in early time to give higher spatial frequency components at higher detail. Modifications of filter 61 and filter 63 are shown in FIGS. 5(c) and 5(d). The spatial filters can be hard filters made of materials which can block light. For example, filters 61 and 63 may be hard filters having a hole size whose radius r is between 0.25 mm to 10 mm. The filters can also be soft filters, not totally opaque, created by optical methods or liquid crystal controlled by computers. The change of the optical density of the spatial filters in turn alters the temporal profiles of light pulses from scattering media in a controllable way.

Figure 6A:
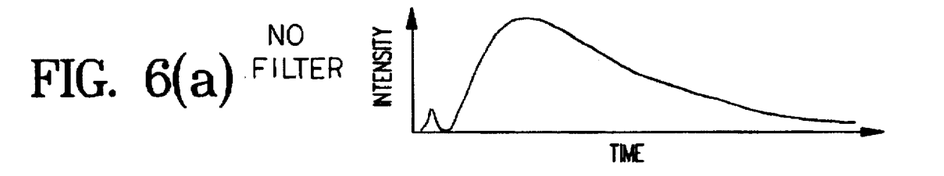
FIG. 6(a) through 6(e) are graphs of the signal profiles of scattered light in time using the spatial Fourier filters shown in FIGS. 5(a) through 5(d). Also are shown the filters for each one of the graphs.
Figure 6B:
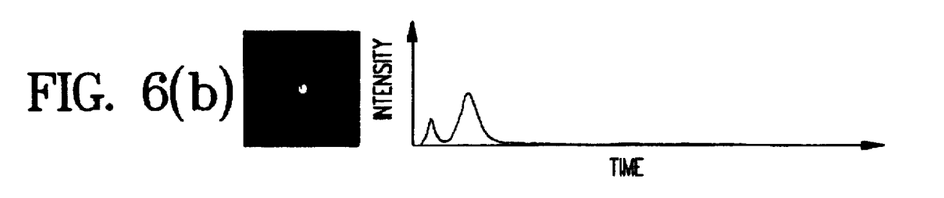
Figure 6C:
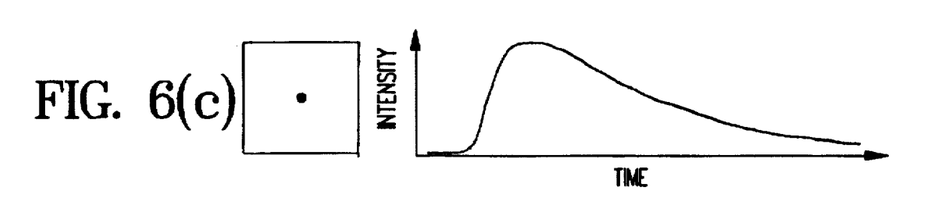
Figure 6D:
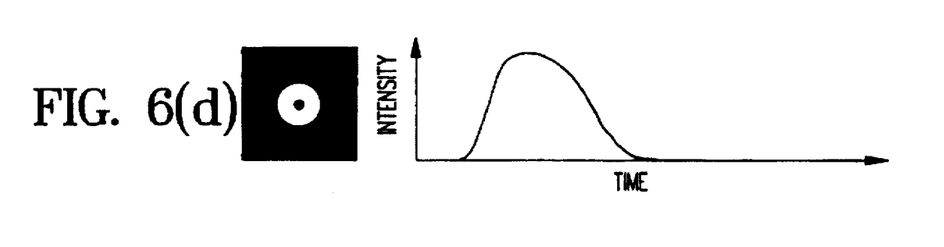
Figure 6E:
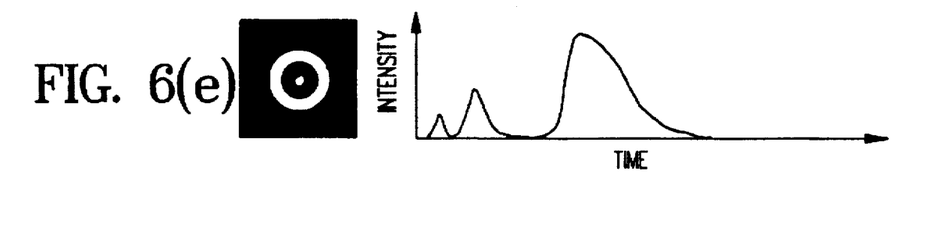

Scattered light at different times can be selected using different shaped spatial filters at the Fourier plane. Examples are given in FIGS. 6(a) through 6(e). FIG. 6(a) displays a temporal profile of a light pulse propagated through a highly scattering/turbid medium without spatial filters placed at the Fourier plane. When a small aperture is placed at the Fourier plane, the diffusive light at later time will be removed and the ballistic and snake light in early time will be selected, as shown in FIG. 6(b). When a complementary inverse spatial filter is placed at the Fourier plane, the ballistic and snake light will be removed and diffusive light will be selected, this is shown in FIG. 6(c). The summation of the temporal profiles in FIGS. 6(b) and 6(c) should be the same as the temporal profile displayed in FIG. 6(a) according to Baberet principle. FIGS. 6(d) and 6(e) display the changes of temporal profiles from scattered light pulses using different types of ring-shaped spatial filters where sections in the profile are highlighted. The spatial filter of FIG. 6(d) is a ring-type aperture. The spatial filter of FIG. 6(e) is a combination of a hole-type aperture and a ring-type aperture.

Figure 7:
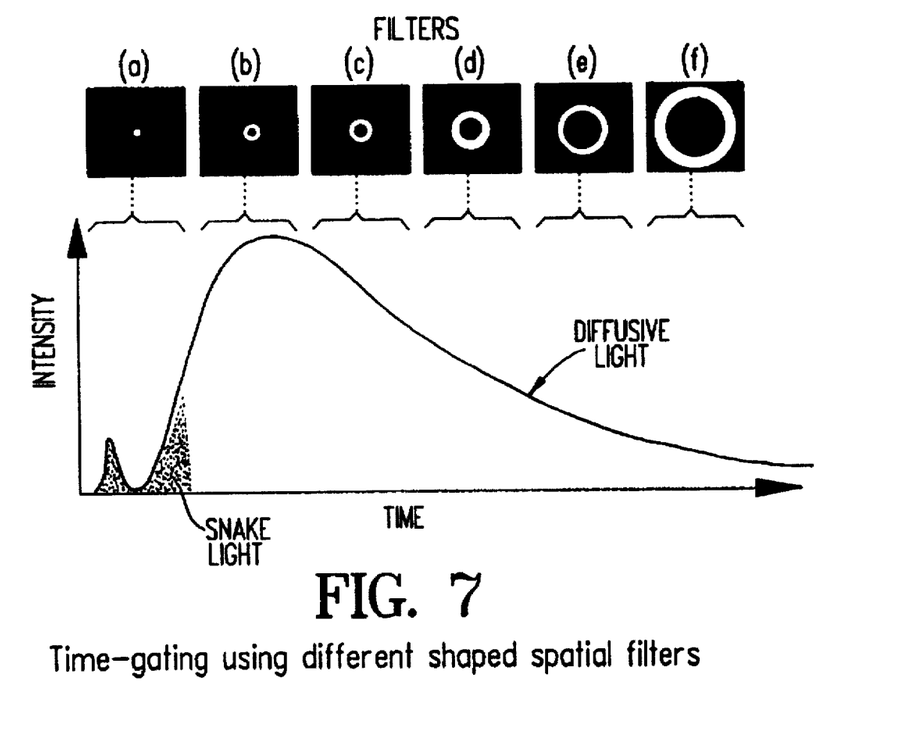
FIG. 7 is a graph showing the time gating using different shaped spatial filters.

FIG. 7 displays the schematic diagram of the time-gating using different shaped spatial filters. The small pin-hole aperture (a) selects the ballistic and snake light in early time. The bigger the radii of the ring-shaped spatial filters are, i.e. filters (b) through (f) the later time portions of the scattered light will be selected.

According to another aspect of this invention time-gating action of Fourier spatial filter for scattered light pulse propagating from a highly scattering/turbid medium can be used for non-medical applications. For example, a Fourier spatial filter can be used for time-resolved imaging of oil droplets in highly scattering soil solution.

Figure 8A:
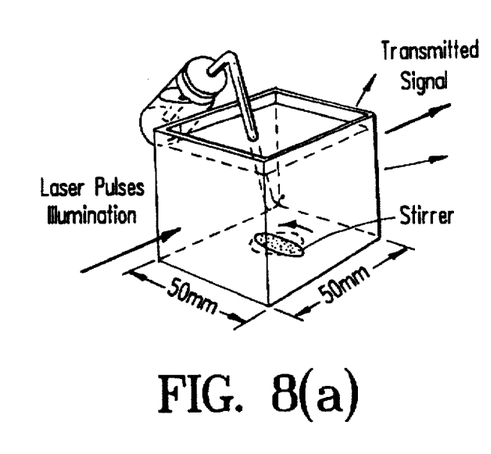
FIGS. 8(a) and 8(b) are an experimental arrangement simulating an oil spill in soil water.
Figure 8B:
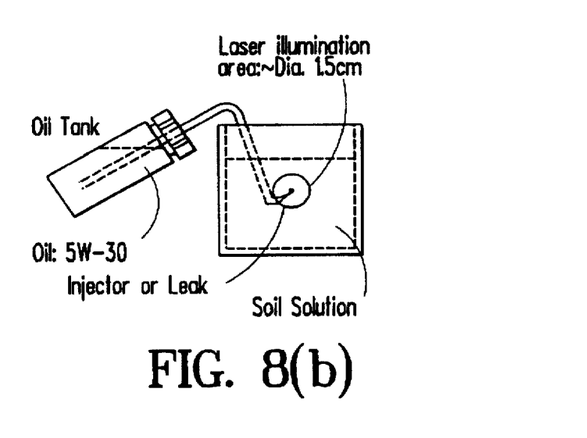
Figure 9:
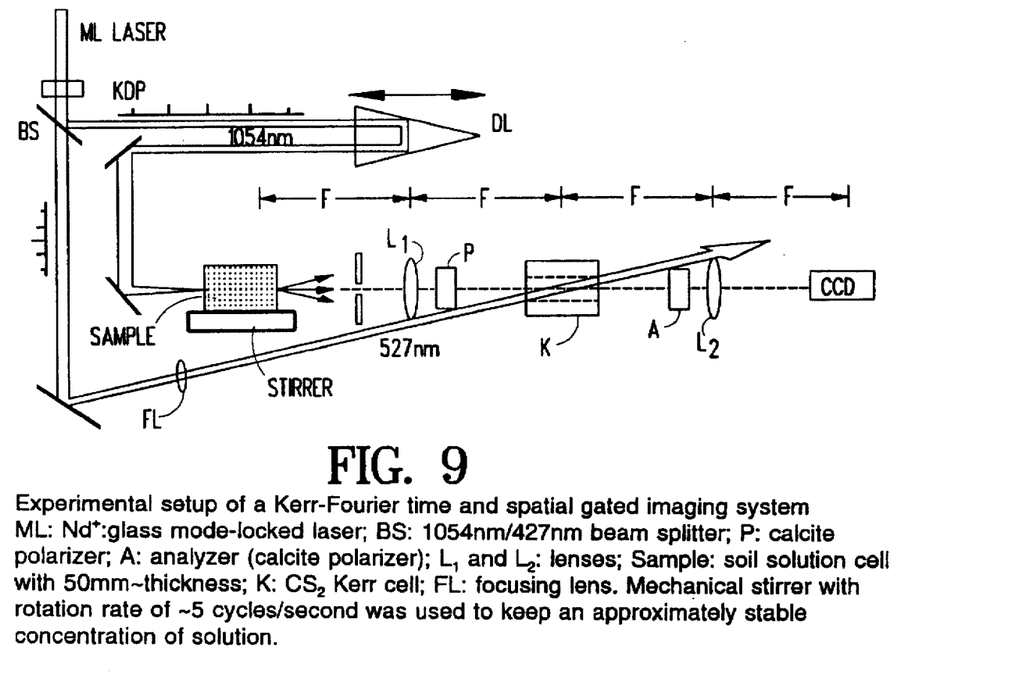
FIG. 9 is an experimental setup of a Kerr-Fourier time and spatial gated imaging system according to this invention.

Experimental 2D images have been obtained of oil droplets in highly scattering soil solution, which simulates pollution caused by oil spills or industrial waste oil into the natural environment. Oil droplets were injected into a highly scattering host soil solution contained in a 50 mm thick cell, as shown in FIG. 8(a). The spatial distribution of the oil droplets within the highly scattering soil solution has been clearly visualized by a time-resolved Kerr-Fourier imaging (FIG. 9). Schematic drawings of the sample phantom and host cell arrangement are shown in FIGS. 8(a) and 8(b). Diluted soil solutions were made by diluting 0.5 ml soil powder into 100 ml distill water. To keep a stable concentration of the soil solution, a mechanical stirrer made by Fisher was used (Flexa-Mix, Model 16). The rotation rate of the mechanical stirrer was at 5 cycles/second to keep an approximately stable concentration solution. The inside dimensions of the host cell were 50×50×50 $mm^3$. The droplets were generated by injecting 5W30 onto the bottom of the host soil solution cell. The transmittance of 5W30 oil at 1054 nm was 61% in 1 cm cell measured by an absorption spectrometer. The measured attenuation coefficient from the Kerr-Fourier (KF) imaging system, shown in FIG. 9 of the host soil solution is 3.5 $mm^{-1}$ at 1054 nm.

The experimental setup to the time-resolved Kerr-Fourier imaging system is shown in FIG. 9. The transmitted shadow signal located at the front focal point plane of the lens was collected and transformed by a lens $L_1$ to the Kerr cell located at the back focal plane. A single shot $Nd^+$:glass mode-locked laser generating 1054-nm 8-ps pulses was used as the probing pulse. The Kerr gate consisting of a pair of crossed calcite polarizers and a $CS_2$ cell. The Kerr cell was placed at the back focal plane of the entrance lens. The second harmonic 527-nm beam was used to actuate the Kerr gate. A 4F Fourier spatial filtering technique coupled with the ultrafast time gated imaging has greatly improved the dynamic range and signal-to-noise ratio. To filter out the diffusive light noise, higher spatial frequency components from diffusive noise are removed at the Fourier plane (F) by the induced Kerr aperture. The spatial dimension of the gating laser pulse radial profile induces a spatial aperture with diameter 2–3 mm at the Kerr cell to effectively remove the higher spatial frequencies. A cooled CCD camera system with 16-bit resolution was used to detect the images of the transmitted signal with $2.5×10^5$ detection pixels.

Figure 10A:
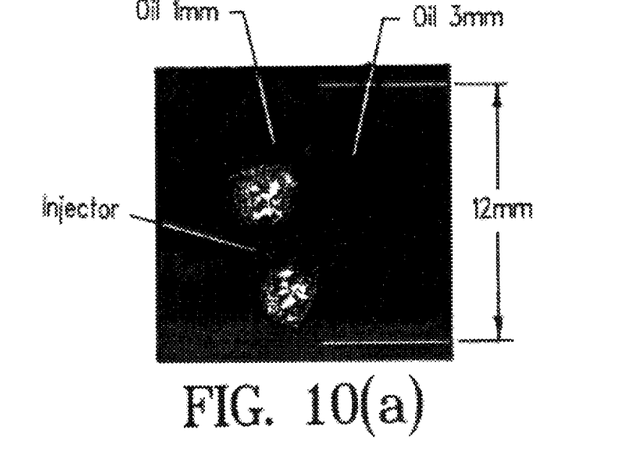
FIG. 10(a) through 10(c) are measured time resolved and CW images of injected oil droplets in a soil solution.
Figure 10B:
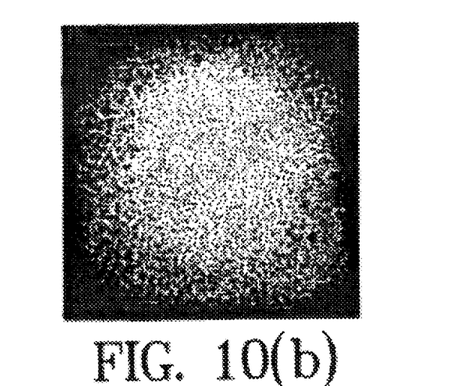
Figure 10C:
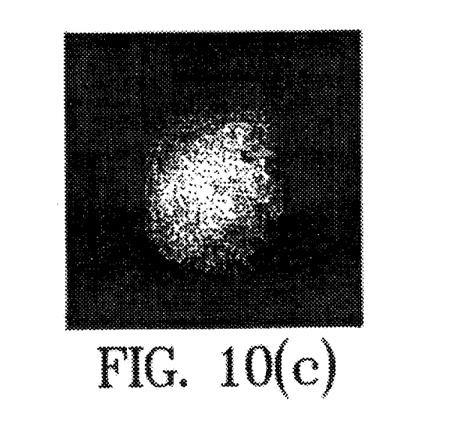

Time resolved KF 2D images of oil droplets injected into the middle of a 50-mm thick host soil solution cell are shown in FIGS. 10(a) at gating time of: T=0, and in FIG. 10(b): T=40 ps. A continuous wave-Fourier (CWF) image is displayed in FIG. 10(c). The image of two oil droplets at the outlet of injector can be seen in FIG. 10(a). Due to the lenslike diffraction effect of the spherically-shaped oil drop, the oil drop is darker except in the center of the ball. The diameter of smaller oil droplet is 1 mm, located at the end of arrow. At a later imaging time (T=40 ps), the image of injector and any possible oil droplets disappear because of blurring effect of the diffusive light as shown in FIG. 10(b). The result in FIG. 10(c) of CWF system shows a blurred image due to diffusive light noise using a non-time resolved space imaging method.

The experiment described above demonstrates that small oil droplets with a millimeter size suspended in a highly scattering soil solution can be spatially determined using an early-time and space gate detection technique and ultrafast laser light source. There are several real-world non-medical applications that these methods can address, such as environmental protection from industrial waste or oil spills, military arena of locating mines in murky water, and commercial applications to diagnose fuel spray in engines, aggregation in chemical or oil transfer lines, and flames in coal burning furnaces.

Some uses for the gate described above as:

Time gate for droplets, oil drops, flames in coal furnaces, jet sprays, micro-size structures in cloudy media such as photographic film, lithographic masks, structures inside cloudy, thermal thick media.

Space gate for droplets, oil drops, flames in coal furnaces, jet sprays, micro-size structures in cloudy media such as photographic film, lithographic masks, structures inside cloudy, thermal, thick media.

Time and space gate for droplets, oil drops, flames in coal furnaces, jet sprays, micro-size structures in cloudy media such as photographic film, lithographic masks, structures inside cloudy, thermal, thick media.

Evaluating and characterizing size and distribution of drops in various media.

Evaluating and characterizing micro and mm size objects in cloudy media.

Enhancing and improving photographic images of items in noisy displays.

Enhancing and improving noisy and hard to see images of objects in highly scattering media found on films, TV displays, signs and human vision.

As can be appreciated, EM radiation (X-ray, NIR, UV) can be used with space gate to time gate a signal from a scattering medium. Space gate detection schemes can be used to significantly improve the contrast of x-ray, optical, uv, and NIR images. Since the signal-to-noise ratio of an image for x-rays depends on the product of the contrast and the square root of the x-ray photon number, an improvement in contrast would allow for the creation of an equal image with less x-ray exposure to patients.

As can be seen, space gate acts as a time slice for each portion of continuous wave electromagnetic (CWEM) radiation and beam used for imaging. Each 10 ps portion CWEM beam can be viewed as pulses, each pulse is temporally sliced by space gating for EM radiation coming from any scattering medium to improve image quality. The size of the aperture selects the temporal gate slice.

What is claimed is:

1. A system for imaging an object in or behind a highly scattering or turbid medium comprising:
   a. means for illuminating said highly scattering medium with a beam of light, the light emerging therefrom consisting of a ballistic component, a snake-like component and a diffuse component, and
   b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis, said mechanical filter being an inverse aperture filter for selectively passing the diffuse component of the emerging light, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

2. A system for imaging an object in or behind a highly scattering or turbid medium comprising:
   a. means for illuminating said highly scattering medium with a beam of light, the light emerging therefrom consisting of a ballistic component, a snake-like component and a diffuse component, and
   b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis and being appropriately constructed to selectively pass one or more of, but not all of, the ballistic component, the snake-like component and the diffuse component of the emerging light, said mechanical filter including an aperture and a ring surrounding said aperture, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

3. A system for imaging an object in or behind a highly scattering or turbid medium comprising:
   a. means for illuminating said highly scattering medium with a beam of light, the light emerging therefrom consisting of a ballistic component, a snake-like component and a diffuse component, and
   b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis and being appropriately constructed to selectively pass one or more of, but not all of, the ballistic component, the snake-like component and the diffuse component of the emerging light, said mechanical filter including a ring having an inner radius r ranging from $r=\frac{1}{4}$ mm to $r=10$ mm, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

4. A system for imaging an object in or behind a highly scattering or turbid medium comprising:
   a. means for illuminating said highly scattering medium with a beam of light, the light emerging therefrom consisting of a ballistic component, a snake-like component and a diffuse component, and
   b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis and being appropriately constructed to selectively pass one or more of, but not all of, the ballistic component, the snake-like component and the diffuse component of the emerging light, said mechanical filter being shaped to include a ring appropriately constructed to select higher frequencies of the emerging light from the highly scattering medium, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

5. A system for imaging an object in or behind a highly scattering or turbid medium comprising:

a. means for illuminating said highly scattering medium with a beam of light, the light emerging therefrom consisting of a ballistic component, a snake-like component and a diffuse component, and b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis and being appropriately constructed to selectively pass one or more of, but not all of, the ballistic component, the snake-like component and the diffuse component of the emerging light, said mechanical filter being used to select the diffuse component of the light emerging from the highly scattering medium, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

6. A system for imaging an object in or behind a highly scattering or turbid medium comprising:

a. means for illuminating said highly scattering medium with a beam of light, the light emerging therefrom consisting of a ballistic component, a snake-like component and a diffuse component, and b. means for forming a temporally gated image of the emerging light, said means including a first lens for focusing the emerging light, said first lens having a back focal plane, a first focal length and an optical axis, a mechanical filter, said mechanical filter being located on said back focal plane in alignment with said optical axis and being appropriately constructed to selectively pass one or more of, but not all of, the ballistic component, the snake-like component and the diffuse component of the emerging light, said mechanical filter being shaped to include a ring for selecting the snake-like component of the light emerging from the highly scattering medium, and a second lens for collimating the light passing through said mechanical filter, said second lens being positioned along said optical axis and having a second focal length and a front focal plane, said mechanical filter being positioned at said front focal plane of said second lens, said second focal length of said second lens being the same as said first focal length of said first lens.

* * * * *